US00RE39359E

(19) United States
(12) Reissued Patent
McGraw et al.

(10) Patent Number: US RE39,359 E
(45) Date of Reissued Patent: Oct. 17, 2006

(54) PORTABLE MUSCLE STIMULATOR WITH PULSE WIDTH CONTROL

(75) Inventors: Michael B. McGraw, Vancouver, WA (US); William A. Rux, Hillsboro, OR (US)

(73) Assignee: International Rehabilitative Science, Inc., Vancouver, WA (US)

(21) Appl. No.: 09/556,389

(22) Filed: Apr. 24, 2000

Related U.S. Patent Documents

Reissue of:
(64) Patent No.: 5,836,995
Issued: Nov. 17, 1998
Appl. No.: 08/806,601
Filed: Feb. 26, 1997

U.S. Applications:
(63) Continuation of application No. 09/290,407, filed on Apr. 13, 1999, now Pat. No. Re. 36,690, which is a continuation of application No. 08/536,924, filed on Sep. 29, 1995, now Pat. No. 5,755,745.

(51) Int. Cl.
*A61N 1/36* (2006.01)

(52) U.S. Cl. ..... 607/48
(58) Field of Classification Search ..... 607/48, 607/59, 66, 72, 63, 64
See application file for complete search history.

(56) References Cited

U.S. PATENT DOCUMENTS 4,622,973 A * 11/1986 Agarwala
4,895,161 A * 1/1990 Cudahy et al.
5,086,778 A * 2/1992 Mueller et al.
5,285,781 A * 2/1994 Brodard
5,549,656 A * 8/1996 Reiss

OTHER PUBLICATIONS

Brochure Entitled: "Introducing a more effective way of prescribing therapy"; Copyright © RS Medical Inc.*

* cited by examiner

*Primary Examiner*—Scott M. Getzow
(74) *Attorney, Agent, or Firm*—Blank Rome, LLP

(57) ABSTRACT

A portable muscle stimulator with removal data storage card is disclosed in which the removable data storage card is secured within the power muscle stimulator on specially designed rail guides which prevent the removable data storage card from being inserted to the power muscle stimulator incorrectly and which ensure that the power muscle stimulator is secured in a removable fashion within the power muscle stimulator. The portable muscle stimulator include a multitude of safety features which are designed to prevent injury to the user while at the same time to ensure that the portable power muscle stimulator is easy to use.

14 Claims, 6 Drawing Sheets

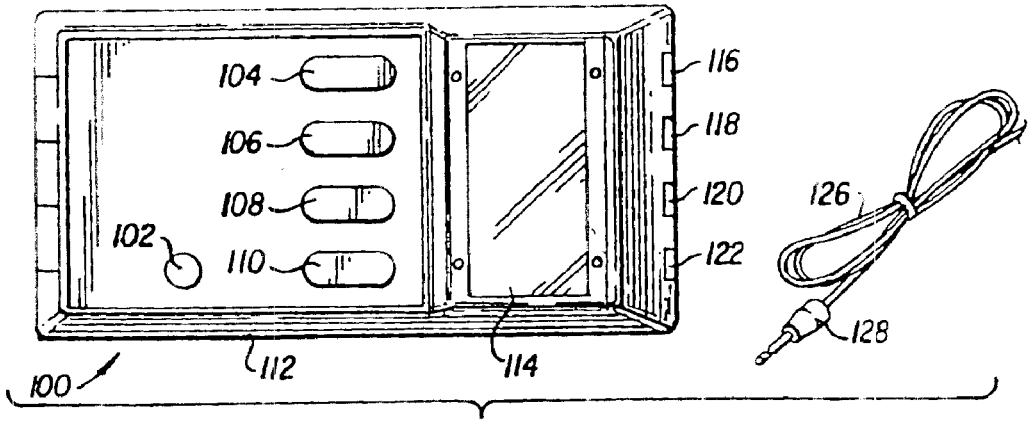
FIG. 1A
FIG. 1B
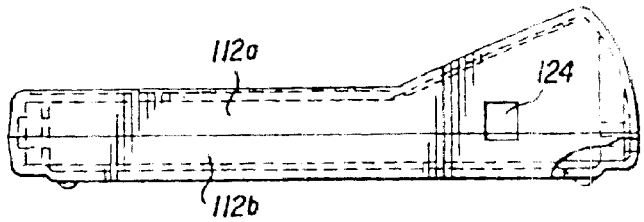
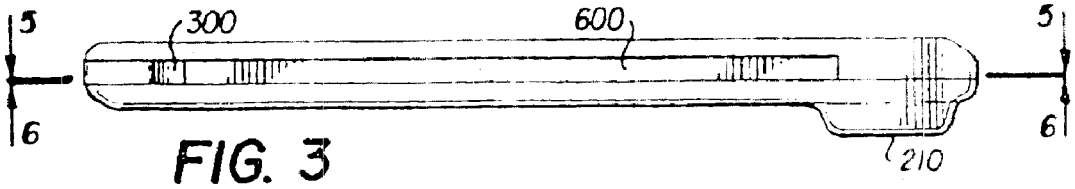
FIG. 3
FIG. 4
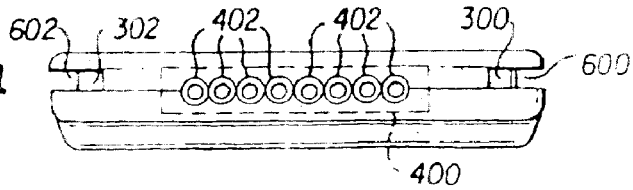

PORTABLE MUSCLE STIMULATOR WITH PULSE WIDTH CONTROL

Matter enclosed in heavy brackets [ ] appears in the original patent but forms no part of this reissue specification; matter printed in italics indicates the additions made by reissue.

This is a continuation of *application Ser. No. 09/290,407, filed Apr. 13, 1999, which is a reissue of application Ser. No. 08/806,601, filed Feb. 26, 1997, now U.S. Pat. No. 5,836, 995, which is a continuation of* application Ser. No. 08/536, 924, filed Sep. 29, 1995 now U.S. Pat. No. 5,755,745.

BACKGROUND OF THE INVENTION

The present invention relates generally to portable muscle stimulators for unsupervised personal use. More particularly, the present invention relates to a method of and system for providing a portable muscle stimulator with a mechanism which provides usage monitoring capability.

With the increasing application of high technology to medical applications, there has been a trend in recent years to providing as much care as possible as well as sophisticated medical treatment outside of hospitals. That trend has resulted in an increase in the amount of surgery as well as other types of medical treatment, such as rehabilitation services, being performed outside of hospitals in, for example, ambulatory surgery centers or rehabilitation centers, respectively.

In order to provide an even more cost effective outcome, technology is being applied to obtain the desired medical outcome with medical equipment that can be utilized in the patient's home. In addition to the cost advantages obtained over providing similar treatment in an outpatient setting, the use of such devices by patients in their homes is also more convenient for the patients, since they do not need to travel to an outpatient center for treatment, and they can initiate their own unsupervised treatment at their convenience.

However, several issues which were not concerns when the treatment services were provided to patients in an outpatient or hospital setting, quickly become concerns when patients supervise their own treatment in their own living areas. First, the device which the patients operate to effectuate their prescribed treatment must be easy to use and must be made as safe to use as possible. Second, it would be desirable to be able to monitor and therefore document the use of the device by the patient, in order to assure that the protocol desired for the patient is being utilized. By obtaining such usage data, the physician/health care providers who have developed and/or prescribed the protocol for use by the patient can be satisfied that the patient is indeed performing the desired protocol and the patient's progress can be measured. In addition, the underwriter of the cost of the treatment can be assured that the patient is actually following the protocol. Such monitoring is important in connection with all of the Class II devices, as they are defined in the Food and Drug Administration's Manual, "Classification Names for Medical Devices and In Vitro Diagnostic Products," such as a powered muscle stimulator as defined in 21 C.F.R. 890.5850. Such Class II devices are regulated and require a prescription by a doctor but do not require a high degree of supervision. Thus, such devices are used personally by the patient for whom they are prescribed without any supervision at the time of use.

SUMMARY AND OBJECTS OF THE INVENTION

In view of the foregoing, it should be apparent that there still exists a need in the art for a method of and apparatus for a portable muscle stimulator which includes a usage monitoring capability for capturing and storing information with respect to the use of the device by a patient. It is, therefore, a primary object of this invention to provide a method of and apparatus for a portable muscle stimulator device having a usage monitoring and storage capability which is characterized by simple electronic circuitry and which has particular application for unsupervised personal use by a patient.

More particularly, it is an object of this invention to provide a powered muscle stimulator device as described above having reliable electronic circuitry and software which can be easily and safely used by an unsupervised patient.

Still more particularly, it is an object of this invention to provide a powered muscle stimulator device which uses a ramp-on/off style of stimulation which is more comfortable to the patient than the previously used abruptly changing stimulation approach.

Another object of the present invention is to provide several additional safety features which both enhance the patient usability and safety of the powered muscle stimulator invention disclosed herein. These features are designed to prevent user error and accidental use and to assure correct operation of the powered muscle stimulator itself.

Briefly described, these and other objects of the invention are accomplished in accordance with its apparatus aspects by providing a removable data storage card which is secured within the powered muscle stimulator on specially designed guide rails which prevent the removable data storage card from being inserted into the powered muscle stimulator incorrectly. The design of the guide rails also functions to removably secure the data storage card in the correct location within the powered muscle stimulator itself. In addition, the pins on the pad cables used with the muscle stimulator are designed with a large diameter so that they cannot be plugged into a typical household 110 volt electrical outlet. In addition, the battery charger cable pin is designed such that it can only plug into the battery charger jack and not into a channel jack, which could damage the powered muscle stimulator.

In its method aspects, the powered muscle stimulator of the present invention is designed to detect if a connection between the pads, cables and the stimulator is faulty and to take appropriate action. The powered muscle stimulator of the present invention is also designed such that a channel output level can be changed only by a single digit at a time, which assures that a rapid increase or decrease in muscle contraction will not be experienced by the user during treatment if the rocker switch was continually depressed.

Other safety features of the powered muscle stimulator include monitoring the battery charger so that none of the channels of the powered muscle stimulator can provide an output to a cable and pad while the battery is being recharged, constantly monitoring the frequency and width of the waveform output by the powered muscle stimulator and taking appropriate action if the waveform changes from the desired pattern, monitoring the liquid crystal display of the powered muscle stimulator and taking appropriate action if the display is not operating properly and constantly monitoring the battery voltage of the powered muscle stimulator and taking appropriate action if the amount of voltage supplied to the microprocessor is incorrect.

An additional safety and treatment feature of the powered muscle stimulator of the present invention is that the stimulus intensity regulated by the patient is the pulse width of the voltage signal which forms the output from each of the channels of the powered muscle stimulator. A ramp on/off type of stimulation is utilized such that the patient experiences a slowly increasing stimuli which is more comfortable than an abruptly changing stimuli used in prior art devices.

With these and other objects, advantages and features of the invention that may become hereinafter apparent, the nature of the invention may be more clearly understood by reference to the following detailed description of the invention, the appended claims, and to the several drawings attached herein.

BRIEF DESCRIPTION OF THE DRAWINGS

FIG. 1A is a drawing of a top view of the powered muscle stimulator of the present invention;

FIG. 1B is a drawing of a side view of the powered muscle stimulator shown in FIG. 1A;

FIG. 3 is a drawing of a side view of the data storage card shown in FIG. 2;

FIG. 4 is a drawing of an end view of the data storage card shown in FIGS. 2 and 3;

DETAILED DESCRIPTION OF THE PREFERRED EMBODIMENT

Figure 2:
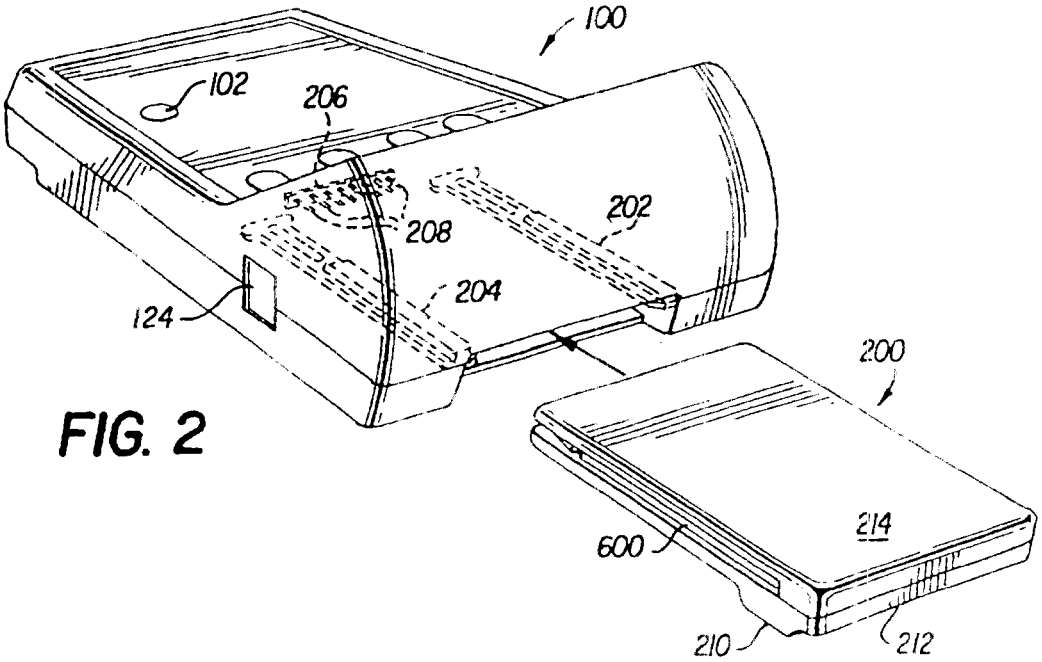
FIG. 2 is a drawing of a front perspective view of the powered muscle stimulator of the present invention showing the data storage card for use therewith.

Referring now in detail to the drawings wherein like parts are designated by like reference numerals throughout, there is illustrated in FIG. 1A a top view of the powered muscle stimulator 100 of the present invention. The powered muscle stimulator 100 includes a power switch 102 and four switches 104–110 for controlling the respective outputs of each of the four isolated channels contained in the powered muscle stimulator 100. An LCD display 114 is provided as a user interface. Four output jacks 116–122 are provided at the front of the case of the powered muscle stimulator 100, a separate jack for each of the output channels. Each of the above-described components, together with the circuitry and a nickel cadmium battery system 1208, as well as other components to be described later herein, are housed within the plastic case or shell 112 of the muscle stimulator 100.

As shown in FIG. 1B, the case or shell 112 of the muscle stimulator 100 may be formed from an upper piece 112a and a lower piece 112b, in order to more easily manufacture the muscle stimulator 100. A jack 124 for connecting the muscle stimulator 100 to a battery charger 1210, may be located on, for example, the right side of the muscle stimulator 100.

The muscle stimulator 100 may be used in a self-administered manner by patients for providing treatments prescribed by physicians and/or other health care providers. The muscle stimulator of the present invention may be used for the relaxation of muscle spasms, for the prevention or retardation of muscle disuse atrophy, for increasing local blood circulation in the legs or other limbs of the patient, for reeducating the leg muscles or other muscles of the patient, for providing immediate post-surgical stimulation of calf muscles of the patient in order to prevent venous thrombosis, or for maintaining or increasing the range of motions of the patient's legs or other limbs.

In order to connect the output jacks 116–122 of the muscle stimulator 100 to the patient, a like plurality of cables (only one cable 126 is shown for purposes of simplicity) is used to make a connection between one of the output jacks and a standard electrode pad (not shown) which contacts the skin of the patient. For safety purposes, the pin 128 of the cable 126 which is inserted into the respective jacks 116–122 in order to connect the electrode pad to the respective output-jack may be formed of such a shape and size that it is not possible to plug the pin 128 into a standard household plug which provides 110 volts of electricity. The pin 128 may preferably be a 2.5 mm diameter female plug.

The powered muscle stimulator 100 of the present invention is a digitally controlled device which provide additional safety features for the user, other than those previously described. The muscle stimulator provides four isolated channels capable of independently treating four separate muscle groups. Each of the four channels has independent output power stages and transformers in order to provide channel separation. The muscle stimulator 100 is battery powered in order to provide portability. The battery power is provided by an internal six volt nickel cadmium battery system 1208, which eliminates the need for patients to monitor and replace batteries. The user interface LCD 114 provides visual feedback to the user. In addition, the circuitry of the muscle stimulator 100 includes a buzzer 1214 having an output which provides audible reinforcement of keystroke actions. Also, each of the isolated channels has a separate intensity control for independently increasing and decreasing the intensity of that channel.

The power switch 102, in addition to powering on the muscle stimulator 100, also serves as an off switch for shutting down the device. The remaining operational functions, such as the contract or on time and relax or off time, treatment time and normal/alternating mode selection have built-in default settings in firmware of 2 seconds, 2 seconds 40 minutes and normal, respectively. However, as will be described later herein, those default settings are easily modified at the time of use, in accordance with the prescription of the user's physician's instructions.

As shown in FIG. 2, the muscle stimulator 100 may be provided with a data storage card 200, the details of which are more fully shown and described in connection with FIGS. 5–11. The data storage card consists primarily of a printed circuit board with a model 24 LC 16B serial EEPROM integrated circuit which is generally connected to various contacts of a header connector 400 having a plurality of contacts 402. In the preferred embodiment, such contacts 402 are female electrical contacts. The header 400 is mounted at one end of the data storage card 200 such that, when the data storage card slides into the muscle stimulator 100 and is positioned by means of the guides 202 and 204 and elongated slots 600 and 602, the contacts 402 of the header 400 fit over the contacts 208 of the header connector 206 mounted inside the muscle stimulator 100.

The data storage card 200 is preferably provided with a "handle" 210 which is formed in the bottom half 212 of the data storage card 200. The top 204 of the data storage card 200, like the bottom 212, is formed from a plastic material. The top 204 and bottom 212 portions may be secured together by means of screws 500 and 502 (shown in FIGS. 5 and 6), glue or other suitable adhesive material. When the data storage card 200 is mounted and properly seated within the muscle stimulator 100, the outside edge of the data storage card 200 serves as a continuation of the normal edge of the muscle stimulator 100.

The bottom portion 212 of the data card 200 has integrally molded elongated slots 600 and 602 which slidably engage with the respective guide rails 204 and 202. Adjacent to the front end of the data storage card 200, a respective stop 300, 302, is provided on each side to ensure a positive stop when the data storage card 200 is properly seated in the muscle stimulator 100.

It should be understood that the elongated slots 600 and 602 are formed as a part of the data card 200 in such a manner that alignment of the data card 200 in the muscle stimulator 100 is ensured because the slots 600 and 602 only allow the data storage card 200 to be inserted into the muscle stimulator 100 with the correct orientation. That is, the elongated or tracking slots 600 and 602 are formed in such a manner that the data storage card 200 cannot be inserted upside down into the muscle stimulator 100.

As shown in the figures, the printed circuit board (not shown) is fully enclosed within the plastic data storage card 200 and covered such that, after the top and bottom portions 212 and 214 of the data storage card shell are secured to each other, all of the internal components contained on the printed circuit board are protected from the outside elements. In addition, the external header connector 400 is designed such that it contains cone shaped guides [where are these shown?] molded into its plastic shape such that it assists in the alignment of the internal header connector 206 mounted in the muscle stimulator 100.

The structure of the storage card 200 is such that it is designed to be used with and removed by the patient from the muscle stimulator 100, or any other similar type of Class II device which a patient uses in an unsupervised manner, mailed to a service bureau for downloading the stored usage information, and replaced with a new data storage card. Typically, a data storage card such as the data storage card 200 disclosed herein, is designed to hold 30–60 days of patient usage information.

The types of information that may be stored in the data card include, for example, the day, month, year and time of day (am or pm) as well as the serial number of and the usage of the muscle stimulator. Such data is stored at the beginning of each data element. Other information stored is whether treatment is present, the length of time in minutes that the muscle stimulator was used, that is, that treatment was provided, the average intensity of the treatment used, the peak intensity of the treatment used, the number of times the treatment was applied within the relevant time period, the initial program mode data, any program changes made by the user and a reserve storage location. In that manner, the maximum number of bytes of data storage for one day could preferably be 26 bytes. During treatment use by the patient, data is accumulated for the treatment period. When the muscle stimulator 100 is turned off, the current treatment data is combined with the present treatment data and stored in an internal temporary storage area 1202.

When the muscle stimulator 100 is next turned on, the clock 1206 which provides the date and time is examined to determine if any 12 hour treatment boundaries have been crossed. If they have, then the temporarily stored data becomes the permanent data for the first 12 hour period beyond the last stored 12 hour period and that data is added to the internal data storage 1202. Next, a determination is made of how many more 12 hour periods have been crossed, and those are stored in the internal data storage 1202 with zero data. Finally, the internally stored data is written to the storage device 1204 contained in the data storage card 200. If no data storage card 200 is present, then no data is written to the card. The data written to the data storage card 200 is written as a block of data using the data stored in the internal storage area 1202. The data is written beginning with the latest stored 12 hour period. That period is used to set the date and the other one time data described above. Then, all available remaining data is written to the data card. However, if there is more data in the internal data storage area 1202 than can be stored on the data card 200, then only the latest data which will fill up the storage element 1204 on the data storage card 200 will be written to that storage element 1204. Thus, for example, if a data storage card 200 has been removed from the muscle stimulator 100 or similar type device, the next time a data storage card 200 is inserted, the new data storage card will be filled immediately with all of the data stored in the internal data storage area 1202, including any "missing" data periods, as long as those "missing" periods are within the data capacity of the data storage card 200.

Figure 9:
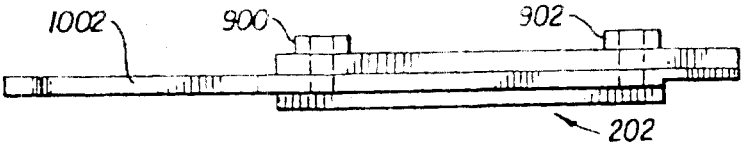
FIG. 9 is a drawing of a side view of a guide rail used in FIG. 7.
Figure 10:
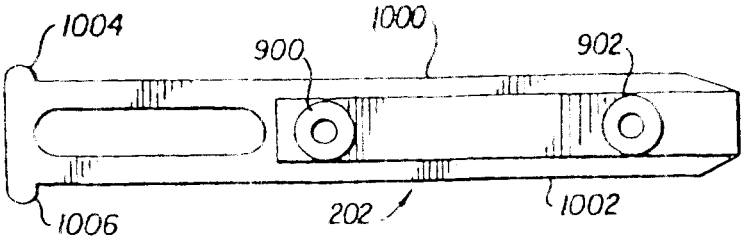
FIG. 10 is a drawing of a top view of the guide rail used for securing the data storage card in the powered muscle stimulator of the present invention.
Figure 5:
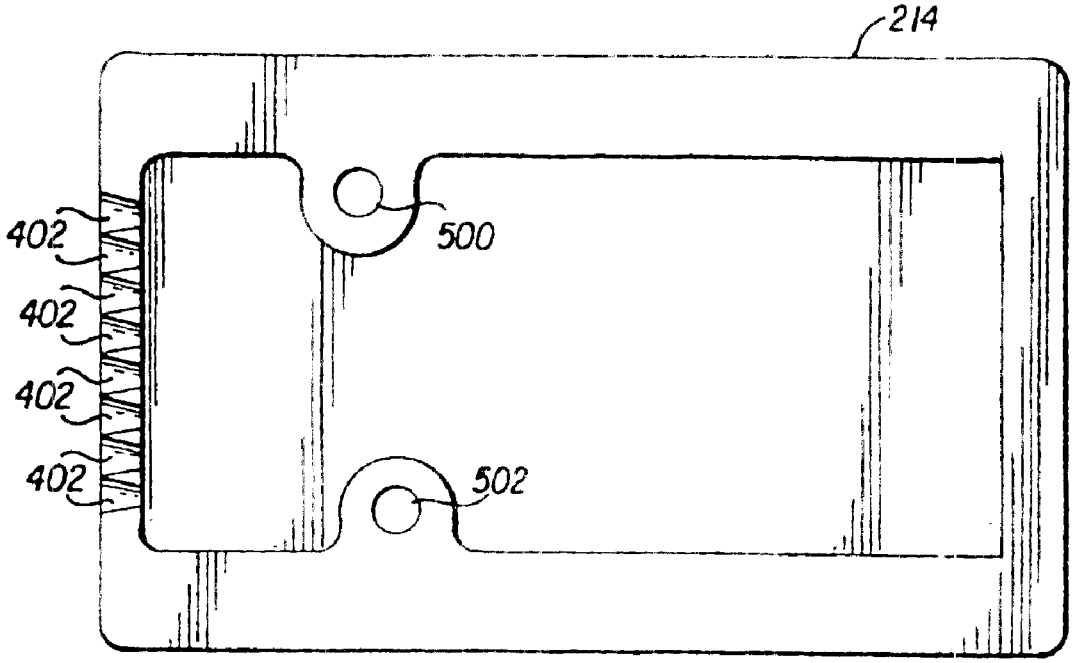
FIG. 5 is a drawing of a cross section of the data storage card of the present invention taken along the line 5—5 of FIG. 3.
Figure 6:
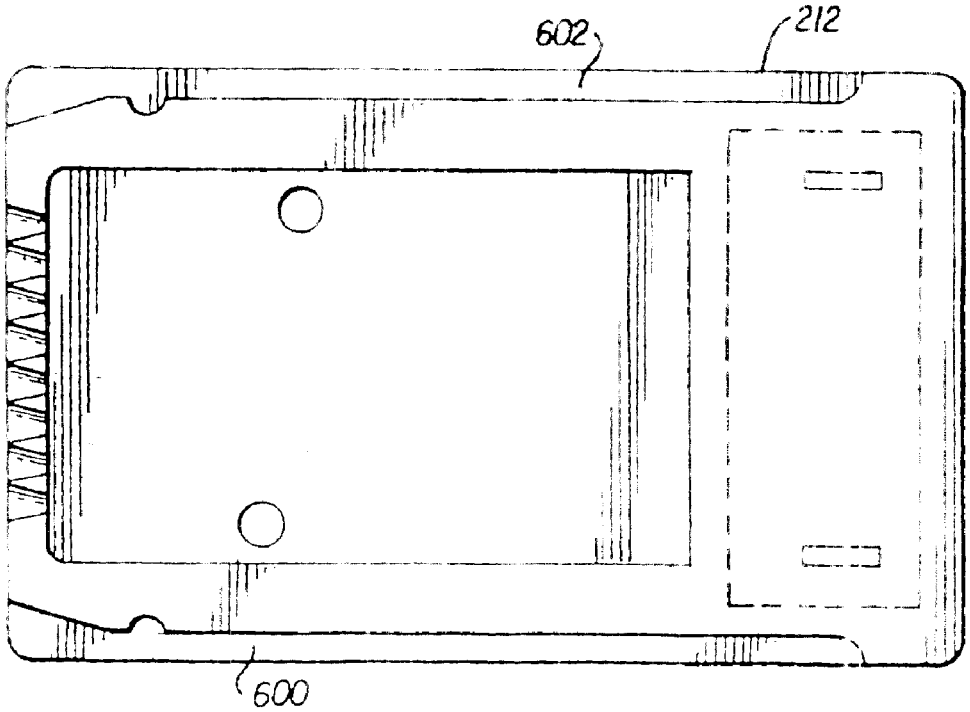
FIG. 6 is a drawing of a cross section of the data storage card of the present invention taken along the line 6—6 of FIG. 3.
Figure 7:
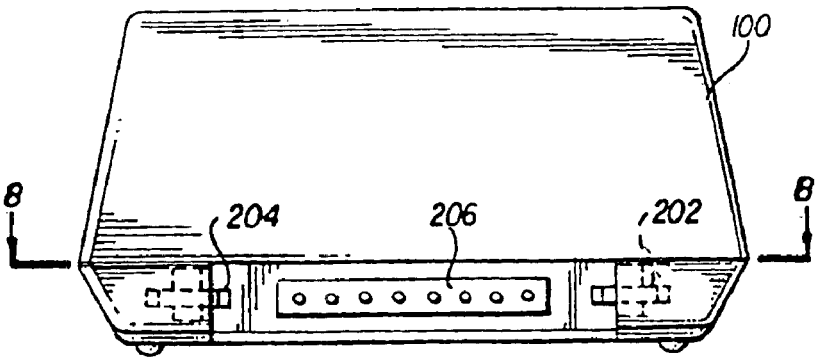
FIG. 7 is a drawing of a front view of the powered muscle stimulator shown in FIG. 1 showing some of the components located inside the stimulator.
Figure 8:
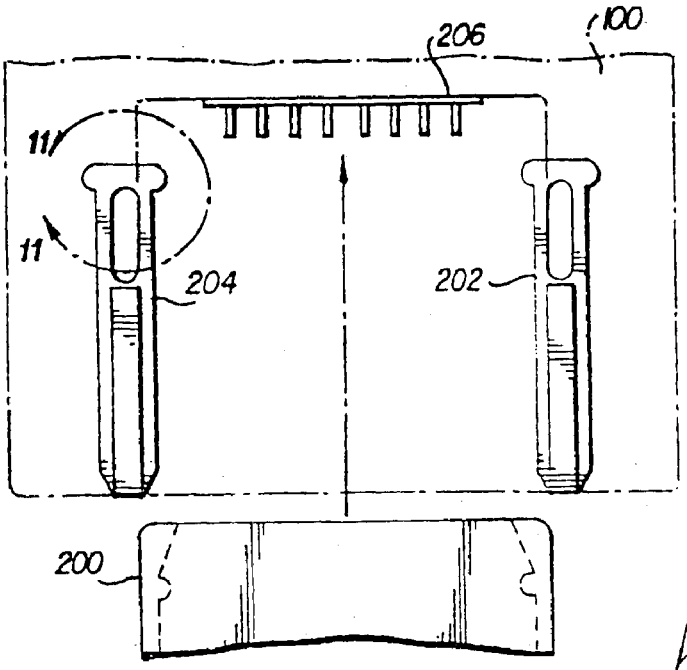
FIG. 8 is a drawing of a section taken along the line 8—8 of FIG. 7.
Figure 11:
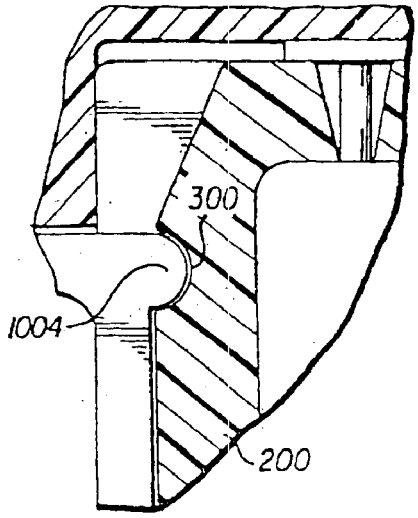
FIG. 11 is a drawing of an enlarged detail of the back portion of the guide rail shown in FIG. 8 designated by circle 11—11.

Turning now to FIGS. 9 and 10, there is shown a side view and top view of the data storage card guides 202, 204, which are constructed as the same piece and mounted inside the muscle stimulator 100 in mirror image fashion using a suitable bracket or other mounting mechanism. Each of the guides includes two mounting holes 900, 902 which may be used in conjunction with screws to attach the guides 200, 204 to suitable mounting brackets (not shown). Each of the guides 200, 204 include two guide surfaces 1000, 1002, one of which is used by each of the guides as the guide surface on which the elongated slots 600, 602 of the data card 200 ride on. Each of the guides 200, 204 are preferably designed to be bidirectional, so it is immaterial which side they are used on. At the inward side of each of the guides 200, 204, an extended rounded portion 1004, 1006 is formed, which is designed to mate with the detents 302, 300 for aligning and securing the data storage card 200 within the muscle stimulator 100. FIGS. 7 and 8 show the guides 202, 204 mounted in the muscle stimulator 100 and their relationship to the internal header connector 206. FIG. 11 shows an enlargement of the alignment and securing mechanism formed by the rounded portion 1004 of the guide 204 and its cooperation with the detent 300 of the data card 200.

Figure 12:
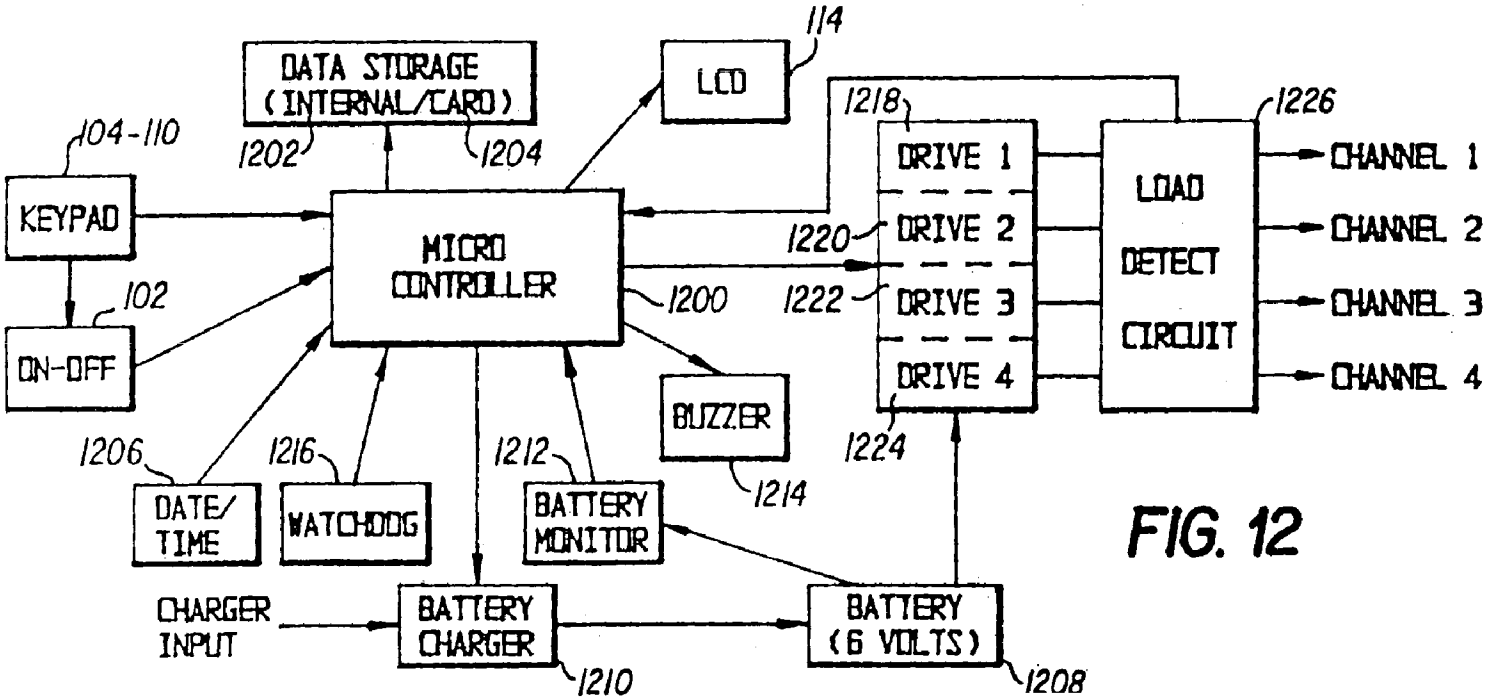
FIG. 12 is a schematic block diagram of the circuitry of the powered muscle stimulator of the present invention.

FIG. 12 is a schematic block diagram of the circuitry used by the powered muscle stimulator 100 of the present invention. The muscle stimulator 100 of the present invention, as previously discussed, is powered by a rechargeable 6 volt nickel cadmium battery system 1208, which is recharged, as will be described later herein, by a battery charger 1210, which may preferably be powered by standard 110 volt household electric current. As a safety feature, the muscle stimulator 100 is designed to be inoperative while the battery system 1208 is being charged. A battery monitor circuit 1212 is connected between the battery system 1208 and the microcontroller 1200 so that the microcontroller can provide an indication to the user by means of the LCD 114 under certain adverse battery conditions as will be described later herein. The microcontroller 1200, as will be described hereafter, serves to control and monitor all of the functions of the muscle stimulator 100.

As previously described, the powered muscle stimulator 100 of the present invention provides four isolated channels 1–4 capable of independently treated four separate muscle groups. Each of the four channels has an independent drive system 1218–1224, which includes independent output power stages and transformers, in order to ensure channel separation. A buzzer 1214 is provided such that audible reinforcement of keystroke actions using the keypad 104–110 is provided to the user.

In operation, the patient first powers up the muscle stimulator 100 using the on/off switch 102. If the patient does not desire to change the settings entered into the internal memory 1202 of the muscle stimulator 100, then the muscle stimulator 100 will be powered up in the previously set mode of operation. The default setting is the normal mode. In that normal mode, all four channels of the muscle stimulator act synchronously, providing the stimulation pulse trains at the same time, although the intensities of each channel are independently controlled. This mode of operation allows the patient to independently treat up to four separate muscle groups simultaneously. If the patient desires, an additional level of control for special situations has been provided, which is termed the alternate mode of operation. In the alternate mode of operation, channels 1 and 2 are operated asynchronously with channels 3 and 4. Thus, when channels 1 and 2 are stimulating the muscles, channels 3 and 4 are off, and when channels 1 and 2 are off, channels 3 and 4 are stimulating the muscles. The set on and off times are the same for all four channels in the normal mode.

During normal operation, the top line of the LCD display 114, which can display up to two lines of 16 characters per line, displays the current settings for the muscle stimulator 100. The bottom line displays the intensity levels selected by the user for each of the four channels. In order to provide visual acknowledgment of the operation of the muscle stimulator, whenever outputs are being sent to a channel, the intensity level has an asterisk (*) displayed beside the intensity level to indicate that the output is being sent to that channel.

If the user wishes to increase the intensity on a certain channel, one of the four rocker type of switches 104–110, which may preferably be designed as an elastomeric keypad, is pushed by the user. One end of each of the switches 104–110 serves to increase the intensity, while the other end of each of the switches serves to decrease the intensity on that channel. When the user is finished a treatment session, the on/off switch 102 is again depressed, turning off the muscle stimulator device 100 at the end of the desired usage.

The four switches 104–110 are also used to change the settings of the muscle stimulator. In order to change the settings, the on/off switch 102 is depressed for five seconds during the start-up sequence, which automatically places the muscle stimulator into the set-up mode. In the set-up mode, each of the rocker switches 104–110 can be used to change one of the four operating parameters (contract time, relax time, treatment time and normal/alternating mode) of the muscle stimulator 100. Once the patient has set the operating parameters of the muscle stimulator as prescribed or desired, the patient then again depresses the on/off switch 102 to store the new parameters. The values set by the patient, based on the prescription and/or physician's instructions, are internally stored in the internal storage 1202 for reuse during future treatments.

As previously described, an external data storage card 200 is used to provide a usage monitoring capability, in conjunction with the internal data storage 1202. The purpose of that monitoring capability is to provide the physician and health care providers, as well as the provider of the muscle stimulator 100, with information documenting the usage of the muscle stimulator 100 by the patient. The cumulative usage of the muscle stimulator 100 by the patient in minutes as well as the average stimulus setting in a 12 hour period (twice per day) is stored and recorded for each channel, initially in the internal data storage 1202. While the internal memory 1202 is preferably capable of storing six months of data, the usage information stored in the memory device 1204 contained in the data storage card 200 is capable of storing only two months of data. The memory device 1204 which forms part of the data storage card 200 is strictly a "write only" device, and allows only the reception and storage of data. No treatment data stored in either the internal data storage 1202 or in the memory 1204 contained on the data storage card 200 can be used for any control functions of the muscle stimulator 100. The muscle stimulator 100 functions normally, whether or not the data storage card 200 is mounted in the muscle stimulator 100. Once the patient is finished with treatment, the muscle stimulator 100 is returned to its manufacturer or other provider and the internal data stored in the internal data storage area 1202 can then be retrieved.

The muscle stimulator 100 of the present invention generates an alternating biphasic asymmetric balanced pulse pattern with a cycle frequency of preferably 71 Hz. The primary pulse has a maximum width of 415 microseconds, followed by the transformer coupled exponential decay back to zero base line. The biphasic pulses alternate direction, resulting in a pulse repetition rate of 142 pulses per second. As previously described, the stimulus intensity is regulated by the patient by pressing the rocker switches 104–110. The voltage level is kept constant. The resulting increase or decrease in stimulus intensity is a result of the increasing or decreasing charge per pulse, which is approximately equal to the pulse width times the pulse height.

Figure 14:
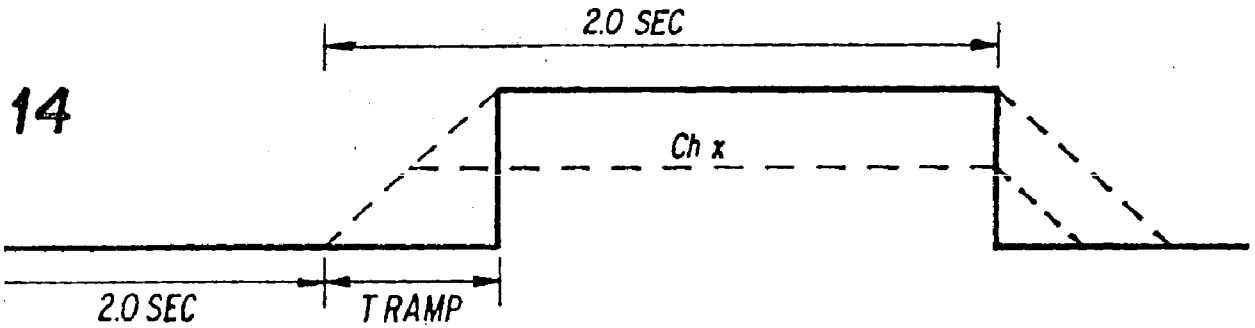
FIG. 14 is a diagram of the ramp structure for each of the output impulses produced by the powered muscle stimulator of the present invention.

The muscle stimulator 100 of the present invention uses a ramp on/off type of stimulation, which increases the pulse width to the desired setting. The pulse generation system of the muscle stimulator 100 preferably consists of an electronic switch such as a logic level Field Effect Transistor, which is controlled by the microcontroller 1200. When a pulse is to be generated, the microcontroller 1200 turns the FET "switch" on. That generates the start of the pulse. When the microcontroller 1200 determines that the pulse is to end, it then turns the FET "switch" off. The FET "switch" applies power from the battery system 1208 directly across the output transformer primary windings which causes the pulse to be generated at the output side of the transformer. Each of the drive circuits 1218–1224 includes such an FET "switch", as well as an output transformer, in a known manner. FIG. 14 illustrates a drawing of a slowly increasing stimuli or ramp used to implement this feature in the muscle stimulator 100 of the present invention.

As already described, the muscle stimulator 100 of the present invention generates a series of pulse trains which generate output pulses for the time period designated by the contract period selected by the user, and then no pulses for the time period designated by the relax period selected by the user. As shown in FIG. 14, at the beginning of each pulse train, the pulse intensity is ramped up by the microcontroller 1200 to allow a smooth transition from no pulses to the pulse intensities specified by the user. Similarly, at the end of the pulse train, the pulses are ramped back down to a zero intensity in order to achieve a smooth release of muscle contractions. The ramping feature is controlled by the microcontroller 1200 and is accomplished by incrementally increasing or decreasing the pulse widths until the desired pulse width is achieved.

The load detect circuit 1226 shown in FIG. 12 may preferably consist of an output voltage signal which is measured across a known load resistance. That signal is amplified and feed back into the analog-to-digital conversion system contained within the microcontroller 1200, which allows a precise measurement of the actual load experienced across the output of the transformer contained in each of the four drive circuits 1218–1224. That measurement allows the microcontroller 1200 to detect both open circuits (that is, no load conditions) and short circuit conditions, which allows the microcontroller 1200 to shut down the control signals going to the pulse generation circuits which form part of the drive circuits 1218–1224. Thus, under open or short circuit conditions, the load detection circuit 1226 operates to shut down the generation of pulses by the muscle stimulator 100.

A watchdog system 1216 is also provided with which to monitor the microcontroller 1200 to ensure that the microcontroller 1200 is operating and issuing instructions. The watchdog system 1216 operates using a "counter". If the "counter" reaches a certain predetermined value, then it operates to shut down the microcontroller 1200 and thus the muscle stimulator 100. During normal operation, the microcontroller 1200 prevents such a shut down from occurring by always resetting the "counter" of the watchdog system 1216 back to zero well before the maximum counter value is reached. In that manner, if the microcontroller 1200 becomes non-operational for any reason, the counter of the watchdog system 1216 would reach the maximum predetermined value and thus shut down the muscle stimulator 100.

Figure 13:
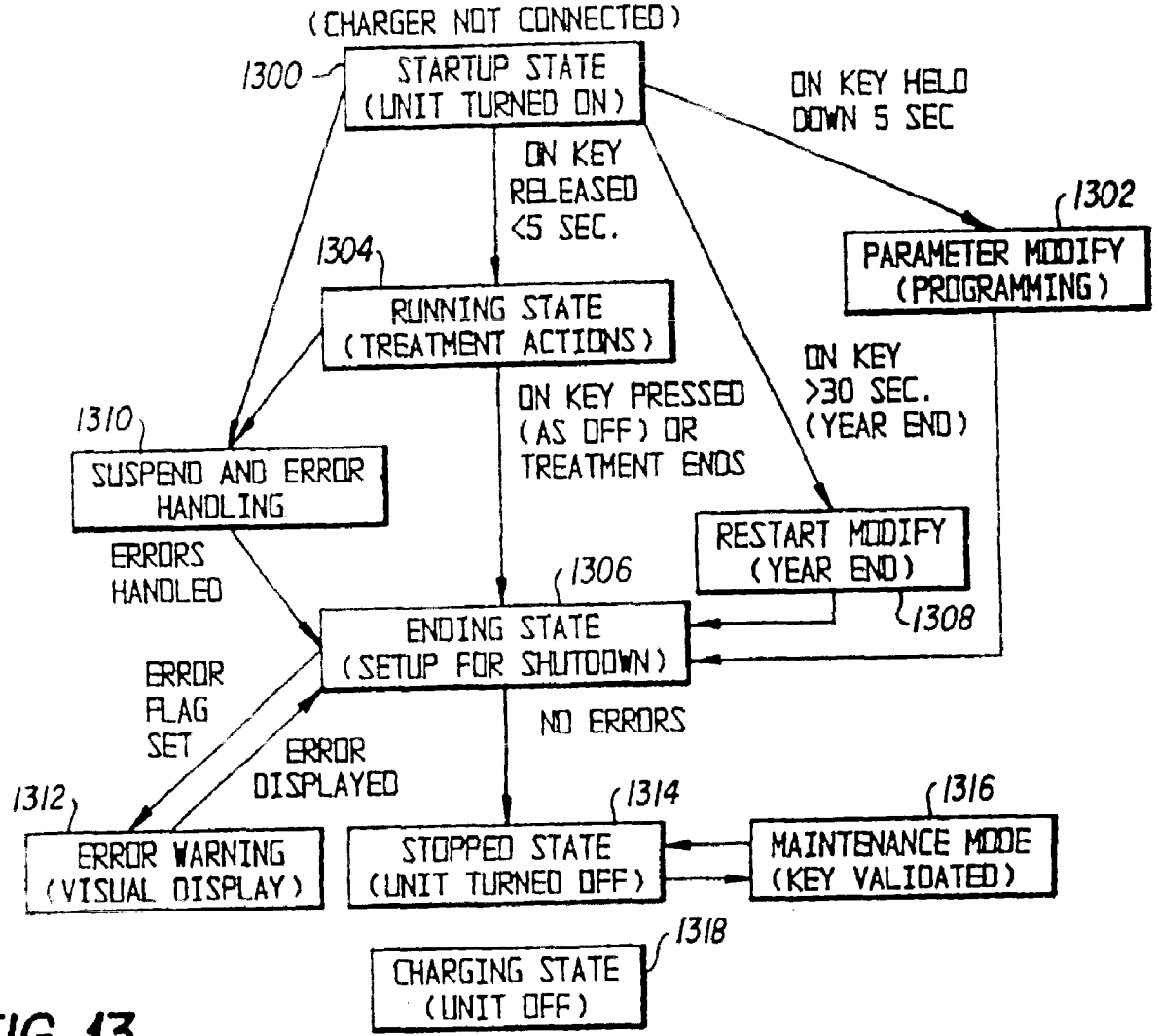
FIG. 13 is a schematic block diagram showing the operation of the software used to operate the powered muscle stimulator of the present invention.

FIG. 13 illustrates, in schematic block diagram form, the firmware permanently stored in the read only memory of the microcontroller 1200 which is used to operate and control the muscle stimulator 100 of the present invention. The firmware is controlled by a Foreground Executive Module, which provides executive control of the muscle stimulator 100 from start-up to shut-down. This module is programmed as a "state machine" such that the firmware controls the operational state of the microcontroller 1200 based on inputs received from the circuitry of the muscle stimulator 100.

As previously described, the primary module which operates the output channel circuits is the pulse generator module, which forms part of the drive circuits 1218–1224. That module is started by the Foreground Executed Module at the startup state 1300, when the on key 102 is depressed. The background pulse generator module is operated in an independent interrupt driven fashion and functions using data supplied by the Foreground Executive Module, which data has been inputted during the parameter modify or programming stage 1302. As previously described, if the on key 102 is released in less than 5 seconds after it is depressed, the muscle stimulator 100 enters the running state 1304, during which the treatment of the patient is provided.

The microcontroller 1200 constantly monitors the operation of the circuitry of the muscle stimulator 100 of the present invention. For example, the firmware monitors the operational frequencies of the background pulse generators which form part of the drives 1218–1224 against an independent frequency to ensure that each of those operational frequencies do not become corrupted. Such monitoring occurs in the running state 1304 and is accomplished through the use of the clock monitoring subsystem of the microcontroller 1200. The clock monitor subsystem of the microcontroller 1200 monitors the frequency of the clock oscillator integrated circuit which determines the actual "speed" or frequency of the operation of the microcontroller 1200 and all the timing actions which it controls. In the event that any of the frequencies become corrupted, the operational state of the firmware shifts to the suspend and error handling state 1310, which displays an error message for the user and then causes the firmware to enter the ending state 1306 which sets up the muscle stimulator for shut-down. The errors are handled in the suspend and error handling state 1310, they are then displayed as a warning on the LCD display 114 in the error warning state 1312 and the muscle stimulator 100 then enters the stop stage 1314, which serves to turn off the muscle stimulator circuitry.

In addition, the firmware also monitors the load on each channel, using the load detect circuit 1226. Again, that monitoring occurs during the running state 1304. In the event that no load is detected, indicating either an open or shorted condition, the firmware again passes to the suspended error handling state 1310, and then passes through the ending state 1306, the error warning state 1312 and enters the stopped state 1314, as previously described. In a similar fashion, the battery system 1208 is monitored by the battery monitor 1212 during the running state 1304 and, in the event it is determined that there will shortly be insufficient power to properly operate the microcontroller 1200, the muscle stimulator 100 is shut down, in a manner similar to that described above in connection with a corrupted background pulse generator frequency or a no load detection condition.

The firmware also accumulates and stores treatment data for each channel, both in the internal memory 1202 and in the memory 1204 of the external data storage card 200. When the patient completes the treatment session, the firmware writes that data to the internal storage 1202 prior to the shut down of the microcontroller 1200. The treatment data is stored on the data storage card 200 by 12 hour time increments. For each 12 hour period, the cumulative patient usage of the muscle stimulator in minutes is recorded, as well as the average stimulus setting. The patient usage data is transferred from the internal data storage 1202 to the storage device 1204 contained on the data storage card during the start-up sequence of the muscle stimulator 100.

The settings for the contract or on time, the relax or off time, the treatment mode (whether normal or alternate) and the length of the treatment are also stored for the user in the microcontroller 1200 memory within the muscle stimulator 100. Those four items are also displayed for the user on the LCD screen 114. Those program mode parameters can be reset at any time by entering the program set-up mode during a start-up sequence of the muscle stimulator 100, in the manner previously discussed. Once the program set-up mode has been entered, the LCD screen 114 displays the program change screen which allows the user, by manipulating the rocker switches 104–110, to change the corresponding program mode parameter displayed on the screen. For example, using the channel 1 switch 104 changes the contract time, using the channel 2 switch 106 changes the relax time, using the channel 3 switch 108 toggles between the normal and alternate modes and using the channel 4 switch 110 increases or decreases the treatment time.

The battery system 1208 is charged during a quick recharge cycle by the battery charger 1210. During the charging cycle, the muscle stimulator is in the charging state 1318, and cannot operate. The battery monitor 1212 as well as the microcontroller 1200 determine the amount of charge needed by the battery system 1208. If the battery system 1208 is sufficiently low, then the battery system will be charged until the battery voltage begins to show a decline, then the charging circuit reverts to a "trickle" charge mode in order to allow maintenance of a fully charged battery at all times.

Additional safety features of the muscle stimulator 100 of the present invention includes a large diameter pin 128 at the end of each of the pad cables 126, such that the pad cable 126 cannot be accidentally plugged into a 110 volt household electrical outlet and cause electrical shock and damage to the pads and cable, a battery charger cable with a pin that plugs only into the battery charger jack 124 thus preventing the battery charger cable from being accidentally plugged into a channel jack, which could damage the muscle stimulator 100 and a plug connection detector (load detect circuit 1226) which is designed to detect if a connection between the pads, cables 126 and the muscle stimulator 100 is faulty. If, after start-up, a faulty connection is detected, the muscle stimulator 100 will not start. If, during operation, a connection becomes loose, the circuitry of the muscle stimulator 100 will be automatically shut-off. The plug connection monitor thus assures the user that all channel connections are good.

The firmware used with the muscle stimulator 100 of the present invention also includes, as a safety feature, a start treatment channel setting. That feature is designed to prevent, at the start of a treatment, a channel output to be set above zero. That assures that the user will not receive an abrupt muscle contraction when starting a treatment. Thus, when starting a treatment, the muscle stimulator 100 begins operation with all channel intensity settings at zero. If a pad is removed from the skin during treatment, the muscle stimulator 100 automatically resets the channel to zero. If a pad cable is unplugged from the muscle stimulator 100 during treatment, the intensity of that channel is reset to zero.

In addition to the start treatment channel setting safety feature, the muscle stimulator 100 of the present invention also includes a channel increase/decrease limit feature, which is designed so that the channel output level can only be changed one digit at a time. Thus, pressing the respective channel rocker switch 104–110 will change the output controlled by that switch by only one digit. That assures that the user will not receive a rapid increase or decrease in muscle contraction during treatment if the rocker switch were continually depressed.

The muscle stimulator 100 of the present invention also includes in firmware a monitor which is designed to constantly monitor the frequency and width of the waveform being applied to each of the pad cables, which is the pattern of output which creates a muscle contraction. If the waveform changes from the pattern it is designed to generate, the muscle stimulator is automatically shut-off. That assures that the user will receive the effective and comfortable contraction designed to be provided by the muscle stimulator 100. As a final safety feature, the muscle stimulator 100 of the present invention is designed to constantly monitor the liquid crystal display 114. If it is determined that the display is not operating properly, then the muscle stimulator 100 is automatically shut-off. In that manner, the patient receives a constant and accurate display of information concerning the operation of the muscle stimulator 100. When the muscle stimulator 100 is first turned on using the switch 102, the LCD 114 displays the default settings for each of the contract time, relax time, mode and treatment time. If those are the prescription settings for the particular patient using that muscle stimulator 100, then there is no need to change the settings. Otherwise, the settings are changed as described previously.

As will be obvious to those of ordinary skill in the art, the data card 200 and its electrical and mechanical structure are such that it can readily be adopted for use in many types of devices, including, for example, any Class II type of device which is designed for unsupervised patient use. Likewise, such a data card could be used in various other types of devices, whether for a supervised patient use or otherwise.

Although only a preferred embodiment is specifically illustrated and described herein, it will be appreciated that many modifications and variations of the present invention are possible in light of the above teachings and within the purview of the appended claims without departing from the spirit and intended scope of the invention.

We claim:

[1. A portable muscle stimulator for generating a plurality of muscle stimulating signals for application to a patient using a plurality of electrodes, comprising:

a plurality of independently driven channels connected respectively to a like plurality of electrodes for independently treating a like plurality of separate muscle groups of a patient, each of said plurality of independently driven channels including its own drive circuit;

a digital data processor connected to each of said drive circuits for each providing a drive control signal for causing each of said drive circuits to generate said plurality of muscle stimulating signals;

each of said drive control signals causing its respective drive circuit to generate a muscle stimulating signal as a series of on and off pulses over a given time period; and said pulses having a predetermined constant voltage and an intensity and a waveform shape such that the beginning of said pulse has a ramp portion from zero to maximum intensity, a middle portion constant at maximum intensity, and an end ramp portion from maximum intensity to zero, such that there is a smooth transition from no pulses to the maximum pulse intensity and then back to no pulses in order to provide smooth muscle contractions and release of contractions.]

[2. The portable muscle stimulator of claim 1, wherein said maximum pulse intensity is selectable by said patient.]

[3. The portable muscle stimulator of claim 2, wherein said patient selects pulse intensity by increasing or decreasing charge per pulse.]

[4. The portable muscle stimulator of claim 1, wherein each of said pulses has a constant voltage level at said maximum intensity portion of said pulses.]

[5. The portable muscle stimulator of claim 1, wherein the time periods during which pulses are generated and not generated are selectable by said patient.]

[6. The portable muscle stimulator of claim 1, wherein pulse intensity for each of said plurality of independently driven channels is separately selectable by said patient.]

[7. The portable muscle stimulator of claim 1, wherein each of said plurality of independently driven channels further includes a load detect circuit connected between each respective electrode and each respective drive circuit, for providing a feedback signal to said digital data processor indicative of an actual load experienced by each respective one of said plurality of drive circuits.]

[8. The portable muscle stimulator of claim 7, wherein said digital data processor receives said feedback signals from each load detect circuit and detects whether short or open circuit conditions exist in each of said plurality of independently driven channels.]

[9. The portable muscle stimulator of claim 8, wherein said digital data processor stops the generation of muscle stimulating signals in any of said independently driven channels in which at least one of an open and short circuit condition is detected.]

[10. The portable muscle stimulator of claim 1, wherein both of said ramp portions of said waveform shape are symmetrical with each other.]

[11. The portable muscle stimulator of claim 1, wherein each of said plurality of independently driven channels is synchronously driven.]

[12. The portable muscle stimulator of claim 1, wherein the maximum intensity of said pulses in each of said independently driven channels is independently controllable by said patient.]

[13. The portable muscle stimulator of claim 1, wherein each pair of said plurality of independently driven channels is synchronously driven within each pair and asynchronously driven with respect to each other pair of driven channels.]

[14. The portable muscle stimulator of claim 1, wherein an average value of the intensity of each of said pulses in each independently driven channel is calculated and stored for later review.]

[15. The portable muscle stimulator of claim 14, wherein said average values are stored in removable data storage which can be removed from said portable muscle stimulator without disabling said stimulator and sent to a remote location for review for compliance with a predetermined treatment plan for said patient.]

[16. A portable muscle stimulator for generating a plurality of muscle stimulating signals for application to a patient using a plurality of electrodes, comprising:

a microcontroller;

a plurality of switches, each connected to be operated by said microcontroller;

a like plurality of output transformers, connected such that power stored in said portable muscle stimulator can be applied to said output transformers by said plurality of switches;

said microcontroller generating a series of pulse trains for generating output pulses by said plurality of output transformers for a first time period predetermined by a contract period selected by said patient and then no pulses for a second time period predetermined by a relaxation period selected by said patient, said output pulses having a predetermined constant voltage; and wherein said microcontroller ramps up the intensity of each pulse at the beginning of each pulse train to an intensity preselected by said patient and then ramps down said intensity to zero at the end of said pulse train in order to allow a smooth transition from zero to maximum intensity to zero intensity, thereby achieving a smooth contraction and release of said patient's muscles.]

[17. The portable muscle stimulator of claim 16, wherein said ramping is controlled by said microcontroller and is accomplished by incrementally increasing or decreasing pulse widths until a desired pulse width is achieved.]

[18. The portable muscle stimulator of claim 16, wherein each of said pulses has a constant voltage level at said maximum intensity portion of said pulses.]

[19. The portable muscle stimulator of claim 16, wherein said patient selects pulse intensity by increasing or decreasing charge per pulse.]

[20. The portable muscle stimulator of claim 16, wherein both said ramp up and said ramp down of said intensity produce symmetrical ramp waveforms.]

[21. A portable muscle stimulator for generating a plurality of muscle stimulating signals for application to a patient using a plurality of electrodes, comprising:

at least three independently driven channels connected respectively to a like plurality of electrodes for independently treating a like plurality of separate muscle groups of a patient, each of said plurality of independently driven channels including its own drive circuit;

a digital data processor connected to each of said drive circuits for each providing a drive control signal for causing each of said drive circuits to generate said plurality of muscle stimulating signals;

each of said drive control signals causing its respective drive circuit to generate a muscle stimulating signal as a series of on and off pulses over a given time period; and said pulses having an intensity and a waveform shape such that the beginning of said pulse has a ramp portion from zero to maximum intensity, a middle portion constant at maximum intensity, and an end ramp portion from maximum intensity to zero, such that there is a smooth transition from no pulses to the maximum pulse intensity and then back to no pulses in order to provide smooth muscle contractions and release of contractions.]

[22. The portable muscle stimulator of claim 21, wherein said maximum pulse intensity is selectable by said patient.]

[23. The portable muscle stimulator of claim 22, wherein said patient selects pulse intensity by increasing or decreasing charge per pulse.]

[24. The portable muscle stimulator of claim 21, wherein each of said pulses has a constant voltage level at said maximum intensity portion of said pulses.]

[25. The portable muscle stimulator of claim 21, wherein the time periods during which pulses are generated and not generated are selectable by said patient.]

[26. The portable muscle stimulator of claim 21, wherein pulse intensity for each of said at least three independently driven channels is separately selectable by said patient.]

[27. The portable muscle stimulator of claim 21, wherein each of said at least three independently driven channels further includes a load detect circuit connected between each respective electrode and each respective drive circuit, for providing a feedback signal to said digital data processor indicative of an actual load experienced by each respective one of said plurality of drive circuits.]

[28. The portable muscle stimulator of claim 27, wherein said digital data processor receives said feedback signals from each load detect circuit and detects whether short or open circuit conditions exist in each of said at least three independently driven channels.]

[29. The portable muscle stimulator of claim 28, wherein said digital data processor stops the generation of muscle stimulating signals in any of said independently driven channels in which at least one of an open and short circuit condition is detected.]

[30. The portable muscle stimulator of claim 21, wherein both of said ramp portions of said waveform shape are symmetrical with each other.]

[31. The portable muscle stimulator of claim 21, wherein each of said at least three independently driven channels is synchronously driven.]

[32. The portable muscle stimulator of claim 21, wherein the maximum intensity of said pulses in each of said independently driven channels is independently controllable by said patient.]

[33. The portable muscle stimulator of claim 21, having four independently driven channels operated in pairs, wherein each of said independently driven channels is synchronously driven within each pair and asynchronously driven with respect to the other pair of driven channels.]

[34. The portable muscle stimulator of claim 21, wherein an average value of the intensity of each of said pulses in each independently driven channel is calculated and stored for later review.]

[35. The portable muscle stimulator of claim 34, wherein said average values are stored in removable data storage which can be removed from said portable muscle stimulator without disabling said stimulator and sent to a remote location for review for compliance with a predetermined treatment plan for said patient.]

[36. The portable muscle stimulator of claim 21, wherein said pulses have a predetermined constant voltage.]

[37. A portable muscle stimulator for generating a plurality of muscle stimulating signals for application to a patient using a plurality of electrodes, comprising:

a plurality of independently driven channels connected respectively to a like plurality of electrodes for independently treating a like plurality of separate muscle groups of a patient, each of said plurality of independently driven channels including its own drive circuit;

a digital data processor connected to each of said drive circuits for each providing a drive control signal for causing each of said drive circuits to generate said plurality of muscle stimulating signals;

each of said drive control signals causing its respective drive circuit to generate a muscle stimulating signal as a series of on and off pulses over a given time period; and said pulses having an intensity controlled by increasing or decreasing charge per pulse and a waveform shape such that the beginning of said pulse has a ramp portion from zero to maximum intensity, a middle portion constant at maximum intensity, and an end ramp portion from maximum intensity to zero, such that there is a smooth transition from no pulses to the maximum pulse intensity and then back to no pulses in order to provide smooth muscle contractions and release of contractions.]

[38. A portable muscle stimulator for generating a plurality of muscle stimulating signals for application to a patient using a plurality of electrodes, comprising:

a plurality of independently driven channels connected respectively to a like plurality of electrodes for independently treating a like plurality of separate muscle groups of a patient, each of said plurality of independently driven channels including its own drive circuit;

a digital data processor connected to each of said drive circuits for each providing a drive control signal for causing each of said drive circuits to generate said plurality of muscle stimulating signals;

each of said plurality of independently driven channels further including a load detect circuit connected between each respective electrode and each respective drive circuit, for providing a feedback signal to said digital data processor indicative of an actual load experienced by each respective one of said plurality of drive circuits;

each of said drive control signals causing its respective drive circuit to generate a muscle stimulating signal as a series of on and off pulses over a given time period; and said pulses having an intensity and a waveform shape such that the beginning of said pulse has a ramp portion from zero to maximum intensity, a middle portion constant at maximum intensity, and an end ramp portion from maximum intensity to zero, such that there is a smooth transition from no pulses to the maximum pulse intensity and then back to no pulses in order to provide smooth muscle contractions and release of contractions.]

[39. The portable muscle stimulator of claim 38, wherein said digital data processor receives said feedback signals from each load detect circuit and detects whether short or open circuit conditions exist in each of said plurality of independently driven channels.]

[40. The portable muscle stimulator of claim 39, wherein said digital data processor stops the generation of muscle stimulating signals in any of said independently driven channels in which at least one of an open and short circuit condition is detected.]

[41. A portable muscle stimulator for generating a plurality of muscle stimulating signals for application to a patient using a plurality of electrodes, comprising:

a plurality of independently driven channels connected respectively to a like plurality of electrodes for independently treating a like plurality of separate muscle groups of a patient, each of said plurality of independently driven channels including its own drive circuit;

a digital data processor connected to each of said drive circuits for each providing a drive control signal for causing each of said drive circuits to generate said plurality of muscle stimulating signals;

said digital data processor calculating and storing for later review an average value of the intensity of each of said pulses in each independently driven channel;

each of said drive control signals causing its respective drive circuit to generate a muscle stimulating signal as a series of on and off pulses over a given time period; and said pulses having an intensity and a waveform shape such that the beginning of said pulse has a ramp portion from zero to maximum intensity, a middle portion constant at maximum intensity, and an end ramp portion from maximum intensity to zero, such that there is a smooth transition from no pulses to the maximum pulse intensity and then back to no pulses in order to provide smooth muscle contractions and release of contractions.]

[42. The portable muscle stimulator of claim 41, wherein said average values are stored in removable data storage which can be removed from said portable muscle stimulator without disabling said stimulator and sent to a remote location for review for compliance with a predetermined treatment plan for said patient.]

*43. A device for use by a patient in an unsupervised manner, the device comprising:*

*a removable data storage for storing data relating to at least one of usage and operation of a Class II device by the patient; and*

*a header for communicating with the removable data storage to retrieve the data relating to said at least one of the usage and the operation of the Class II device;*

*wherein the removable data storage does not contain information used to control the Class II device.*

*44. The device of claim 43, wherein said removable data storage comprises a card including storage media.*

*45. The device of claim 44, wherein the stored data can be extracted for review.*

*46. The device of claim 44, wherein:*

*the card comprises contacts; and*

*the header comprises female contacts for making electrical contact with the contacts of the card to retrieve the data.*

*47. The device of claim 44, wherein the storage media comprise an integrated circuit for storing the data.*

*48. The device of claim 47, wherein the integrated circuit is an EEPROM.*

*49. The device of claim 43, wherein the data comprise data for 30–60 days of use of the Class II device by the patient.*

*50. The device of claim 43, wherein the data comprise at least one date and time of usage of the Class II device.*

*51. The device of claim 43, wherein the data comprise a serial number of the Class II device.*

*52. The device of claim 43, wherein the data comprise a length of time in which the patient used the Class II device.*

*53. The device of claim 43, wherein the data comprise an average intensity of treatment by the Class II device.*

*54. The device of claim 43, wherein the data comprise a peak intensity of treatment by the Class II device.*

*55. The device of claim 43, wherein the data comprise data for each of a plurality of independently driven channels of the Class II device.*

*56. The device of claim 55, wherein the data for each of the plurality of independently driven channels comprise an average pulse intensity in each of the plurality of independently driven channels.*

* * * * *